United States Patent [19]

Gootjes

[11] 4,003,932
[45] Jan. 18, 1977

[54] AMINOALKYLETHERS

[75] Inventor: Johan Gootjes, Heerhugowaard, Netherlands

[73] Assignee: Gist-Brocades N.V., Netherlands

[22] Filed: Mar. 6, 1973

[21] Appl. No.: 338,621

[30] Foreign Application Priority Data

Mar. 7, 1972 United Kingdom ............ 10543/72

[52] U.S. Cl. ...................... 260/570 R; 260/326 R; 260/465 F; 260/473 A; 260/501.18; 260/559 P; 260/562 P; 424/316; 424/330

[51] Int. Cl.² ...................................... C07C 93/06

[58] Field of Search ................. 260/570 R, 501.18; 424/330

[56] References Cited

UNITED STATES PATENTS

| | | | |
|---|---|---|---|
| 2,527,963 | 10/1950 | Rieveschl | 260/570 X |
| 3,266,988 | 8/1966 | Sannders | 260/570 X |
| 3,565,955 | 2/1971 | Ehrhart et al. | 260/570 |
| 3,666,811 | 5/1972 | Stelt | 260/570 |

OTHER PUBLICATIONS

Burger, "Medicinal Chemistry", 2nd Ed. pp. 42–43 and 505–506 (1960).

*Primary Examiner*—Robert V. Hines
*Attorney, Agent, or Firm*—Robert E. Burns; Emmanuel J. Lobato; Bruce L. Adams

[57] ABSTRACT

Diphenylmethoxyethylamines of the general formula

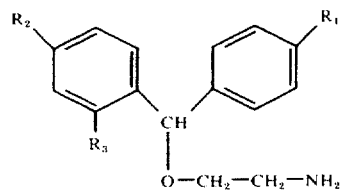

II in which $R_1$ represents a fluorine, bromine or chlorine atom, $R_2$ represents a hydrogen or fluorine atom and $R_3$ represents a hydrogen, fluorine or chlorine atom, with the provisos that $R_3$ is a hydrogen atom when $R_2$ is a fluorine atom, $R_1$ is a fluorine atom when $R_3$ is a chlorine atom and $R_1$ is a fluorine or bromine atom when $R_2$ and $R_3$ both are hydrogen atoms, and their non-toxic acid addition salts are disclosed. The compounds have dopaminergic properties and their use is indicated for treating the Parkinson syndrome. Compositions for such use are disclosed.

5 Claims, No Drawings

AMINOALKYLETHERS

This invention relates to therapeutically useful basic ethers and acid addition salts thereof, to processes for their preparation and to pharmaceutical compositions containing them.

The ethers with which the present invention is concerned are substituted diphenylmethoxyethylamines. This type of compounds is known i.a. from British patent specification No. 1,219,609, French patent specification 1,377,277 and U.S. Pat. No. 3,032,556. Said patents disclose compounds encompassed by the general formula

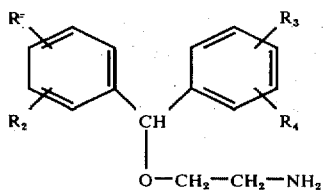

in which the symbols $R_1$-$R_4$ are the same or different and each represents a hydrogen or halogen atom or a lower alkyl group.

The ethers of formula I have been disclosed as being useful only as intermediates for therapeutically useful compounds. It has now unexpectedly be found that certain compounds within formula I and having the structure

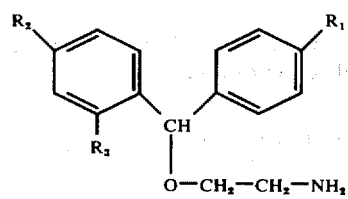

in which $R_1$ represents a fluorine, bromine or chlorine atom, $R_2$ represents a hydrogen or fluorine atom and $R_3$ represents a hydrogen, fluorine or chlorine atom, with the provisos that $R_3$ is a hydrogen atom when $R_2$ is a fluorine atom and $R_1$ is a fluorine atom when $R_3$ is a chlorine atom, and their acid addition salts possess therapeutic properties in their own right.

The ethers of general formula II except for the compound in which $R_1$ is a chlorine atom and $R_2$ and $R_3$ are hydrogen atoms, i.e. 2-[α-(p-chlorophenyl)benzyloxy]-ethylamine, are new compounds and as such they and acid addition salts thereof constitute the most important feature of the invention.

The ethers of formula II show valuable biological activities, indicating that the compounds have dopaminergic properties. The compounds induce so-called bizarre social behaviour in rats (A. J. J. C. Lammers and J. M. van Rossum, Eur. J. Pharmacol. 5, 103–106 (1968)). They possess reserpine and α-methyl-p-tyrosine antagonizing properties and they cause turning behaviour in rats with one-sided striatal lesions (N. E. Anders et. al., Acta Pharmacol. et Toxicol., 24, 263–274 (1966)). The haloperidol-induced catalapsis, which is of dopaminergic origin, is more strongly antagonized that the catalapsis caused by chlorpromazine, which is of a more adrenergic type. These activities are typical for compounds like L-Dopa and apomorphine. The ethers of formula II, however, do not cause vomiting when administered to dogs. The ethers of formula II are therefore useful agents in combatting Parkinson's disease.

The most active — and therefore preferred — ethers are those of formula II in which $R_2$ or $R_3$ represents a fluorine atom and $R_1$ represents a fluorine or chlorine atom, and particularly the compounds 2-[bis(p-fluorophenyl)methoxy]ethylamine, 2-{[p-chloro-α-(p-fluorophenyl)-benzyl]oxy ethylamine } and 2-{[o-fluoro-α-(p-fluorophenyl)-benzyl]oxy} ethylamine and their acid addition salts.

For use as therapeutics the ethers of formula II may be used as bases or as acid addition salts containing pharaceutically acceptable non-toxic anions, e.g. the hydrohalides, sulphates, oxalates, tartrates, fumarates, citrates, maleates, succinates and lactates.

The bases or non-toxic acid addition salts thereof may be administered orally or parenterally in a pharmacologically acceptable carrier according to accepted pharmaceutical practice. In adults the oral dosage will be from 10 to 100 mg daily.

According to a feature of the invention, the ethers of formula II are prepared by removing by a method known per se the phthaloyl group from a phthalimide derivative of the general formula:

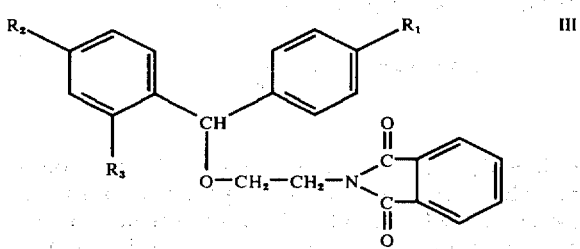

in which the R symbols are as hereinbefore defined. Preferably the phthalimide derivative is reacted with hydroxylamine, or an acid addition salt thereof, at room temperature in the presence of an alkoxide, such as sodium methoxide, dissolved in an alcohol, such as methanol or ethanol.

The starting materials of formula III may be prepared by reacting an ether of the general formula:

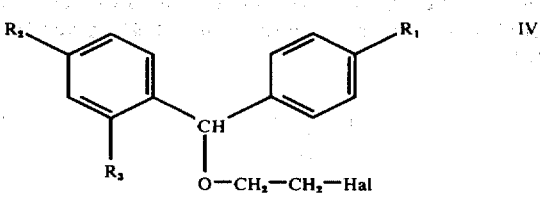

in which Hal represents a halogen atom and the R symbols are as hereinbefore defined, with potassium phthalimide, preferably by refluxing the reactants in a polar solvent capable of dissolving potassium phthalimide, such as dimethylformamide.

According to another feature of the invention, the ethers of formula II are prepared by hydrolyzing an amide of the general formula:

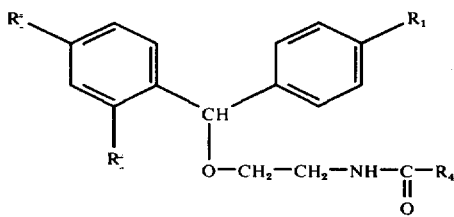

in which $R_4$ represents a hydrogen atom or an alkyl, aryl or aralkyl group, and $R_1$, $R_2$ and $R_3$ are as hereinbefore defined. The reaction is preferably carried out by refluxing the amide in an alcohol, such as ethanol, with a base, such as sodium hydroxide.

The starting materials of formula V may be prepared by reacting a substituted diphenylmethyl chloride of the general formula:

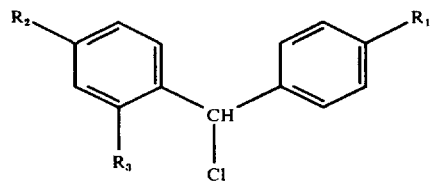

in which the symbols are as hereinbefore defined, with a compound of the general formula:

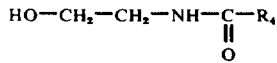

in which $R_4$ is as hereinbefore defined. The reaction is preferably carried out by refluxing the reactants in an inert organic solvent, such as benzene or toluene, in the presence of a base, such as potassium carbonate or a tertiary amine (e.g. triethylamine).

The compounds of formula VII may be obtained by replacing a hydrogen atom of the amino group in aminoethanol by a group

$R_4$ a method known per se for the acylation of primary aminos. The amino alcohol may, for example, be reacted with an ester or acid halide of the general formula:

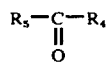

in which $R_5$ represents a halogen atom or an alkoxy group. The reaction may be carried out by refluxing a mixture of the reactants, if necessary dissolved in an inert organic solvent such as benzene or toulene.

According to another feature of the invention, the ethers of formula II are prepared by reacting an ether of formula IV with ammonia. The reaction is preferably carried out by heating the compound of formula IV, dissolved in lower alcohol (e.g. methanol) with a large excess of ammonia in a closed vessel.

According to another feature of the invention, the ethers of formula II are prepared by reducing by a method known per se an amido of the general formula:

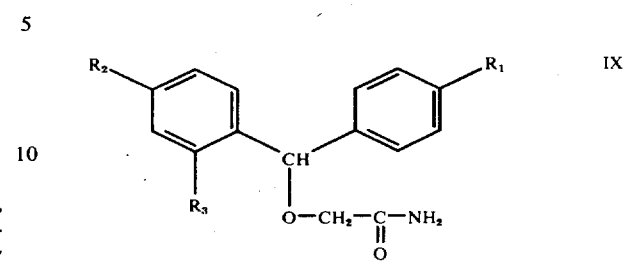

in which the R symbols are as hereinbefore defined. The reduction is preferably effected by reaction of the amide, preferably dissolved in diethyl ether or tetrahydrofuran, with lithium aluminum hydride, followed by decomposition of the complex compound obtained with water.

The starting materials of formula IX may be prepared by reacting a substituted benzhydrol of the general formula:

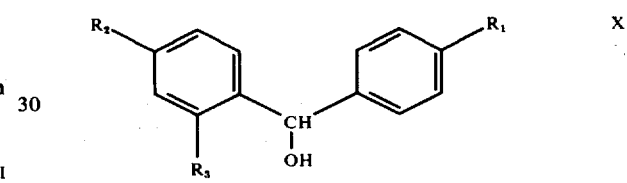

in which the R symbols are as hereinbefore defined, with a compound of the formula:

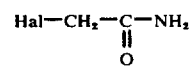

in which Hal is as hereinbefore defined, preferably by heating the reactants in an inert organic solvent, such as benzene or toluene, in the presence of a base, such as sodium carbonate or a tertiary amine (e.g. triethylamine).

The amides of formula IX may also be prepared by reacting an ester of the formula

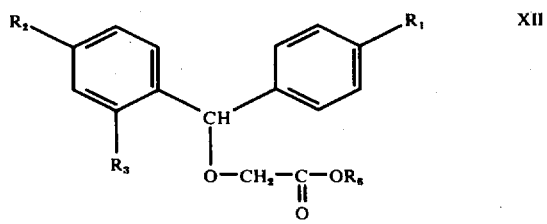

in which $R_6$ represents a lower alkyl group and $R_1$, $R_2$ and $R_3$ are as hereinbefore defined, with ammonia. The ester may, for instance, be kept standing for a considerable time (e.g. 10 to 20 hours) with an excess of ammonia, dissolved in a lower alcohol such as methanol.

According to another feature of the invention, the ethers of formula II are prepared by reducing a nitrile of the general formula

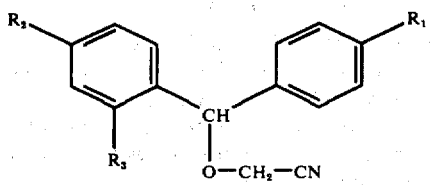

in which $R_1$, $R_2$ and $R_3$ are as hereinbefore defined, by a method known per se for the reduction of a nitrile to a primary amine. The reduction is preferably carried out by refluxing the nitrile in an organic solvent, such as diethyl ether or tetrahydrofuran, with lithium aluminum hydride, followed by decomposition of the complex compound obtained with water.

The starting materials of formula XIII may be prepared by reacting a diphenylmethyl chloride of formula VI with hydroxyacetonitrile, preferably by refluxing the reactants in an inert organic solvent (e.g. benzene or xylene) in the presence of a base, such as sodium carbonate or triethylamine.

The starting materials of formula XIII may also be obtained by dehydrating an amide of formula IX, for instance by refluxing the amide in an inert organic solvent such as toluene or xylene with phosphorus pentoxide.

Acid addition salts of the ethers of formula II may be prepared by methods known per se. For example, the base may be treated with the equivalent amount of the acid in an inert organic solvent, such as diethyl ether.

By the term "methods known per se" as used in the specification is meant methods heretofore used or described in the literature.

The following Examples illustrate the preparation of others of general formula II by aforementioned processes of the present invention.

EXAMPLE I

A mixture of 28.2 g (0.1 mole) of 2-[bis(p-fluorophenyl)methoxy]ethyl chloride and 17 g (1 mole) of ammonia in 187.5 ml of methanol is shaken in an autoclave for a period of 6 hours at 135° C. The reaction mixture is poured into water and extracted with diethyl ether. The extract is acidified with 2N hydrochloric acid. The acid aqueous layer is separated off, made alkaline with 2N sodium hydroxide and extracted with diethyl ether. The extract is dried over potassium carbonate and the ether is distilled off. The residue is distilled, yielding 15.4 g of 2-[bis(p-fluorophenyl)-methoxy]ethylamine, boiling point 130° C/0.2 mm.Hg. The base is dissolved in diethyl ether and an ethereal solution of maleic acid is added. The precipitate is filtered off and crystallised from a mixture of ethanol and diethyl ether. 2-[Bis(p-fluorophenyl)methoxy]ethylamine hydrogen maleate is obtained. Its melting point is 126°–127° C.

EXAMPLE II

A solution of 16.1 g (0.057 mole) of 2-[bis(p-fluorophenyl)methoxy]ethyl chloride and 10.5 g (0.057 mole) of potassium phthalimide in 55 ml of dimethylformamide is refluxed for 2 hours. The mixture is cooled and water is added. The aqueous layer is extracted with toluene and the extract is dried over potassium carbonate and concentrated by evaporation of solvent. The residue consists of N-{2-[bis(p-fluorophenyl)methoxy]-ethyl}phthalimide, m.p. 109.6°–111° C.

A solution of 12.5 g (0.18 mole) of hydroxylamine hydrochloride in 180 ml of ethanol is added to 90 ml of 4N sodium methoxide. The sodium chloride formed is filtered off and a solution of 22 g (0.056 mole) of the aforesaid phthalimide derivative in 120 ml of ethanol is added. The mixture is stirred for 30 minutes. The alcohol is distilled off and the residue is shaken with diethyl ether and water. The ethereal phase is separated off, dried over potassium carbonate and concentrated by evaporation of solvent. The residue is distilled, yielding 2-[bis(p-fluorophenyl)methoxy]-ethylamine, boiling point 120°–126° C/0.15 mm.Hg. The base is dissolved in diethyl ether and ethereal hydrogen chloride is added; the hydrochloride precipitates. The salt is crystallised from ethanol; it melting point is 170°–172° C.

EXAMPLE III

By using the procedure of Example II but substituting the 2-[bis(p-fluorophenyl)methoxy]ethyl chloride by the appropriate compounds of formula IV (with Hal = Cl) the following compounds of general formula II are obtained.

| $R_1$ | $R_2$ | $R_3$ | Salt | Crystallisation solvent | Melting point |
|---|---|---|---|---|---|
| Cl | F | H | Hmal | a | 134–136° C |
| F | H | F | HCl | b | 108–110° C |
| Br | F | H | Hmal | a | 133–135° C |
| Br | H | H | Hmal | a | 134–135° C |
| F | H | H | Hmal | c | 130–132° C |
| Cl | H | F | Hmal | d | 127–129° C |
| Cl | H | H | HCl | e | 147–149° C |

In the foregoing Table "Hmal" is an abbreviation for hydrogen maleate, and the crystallisation solvents are as follows:

a = ethanol, diethyl ether;
b = methanol, diethyl ether, petroleum ether (boiling range 28°–40° C);
c = isopropanol, diethyl ether;
d = ethanol, diethyl ether, petroleum ether (boiling range 28°–40° C);
e = ethanol, diethyl ether, petroleum ether (boiling range 40°–60° C);

EXAMPLE IV

A mixture of 5 g (0.016 mole) of N-{2-[bis(p-fluorophenyl)methoxy]ethyl}acetamide and 4 g (0.1 mole) of sodium hydroxide, dissolved in 25 ml of ethanol, is refluxed for 17 hours. The reaction mixture is cooled and the ethanol is distilled off. The residue is taken up in water and extracted with diethyl ether. The extract is acidified with 2N hydrochloric acid, the aqueous layer is made alkaline with sodium hydroxide and extracted with diethyl ether. The extract is dried over potassium carbonate and the ether is distilled off. The residue is dissolved in the diethyl ether and ethereal hydrogen chloride is added. The precipitate formed is crystallised from ethanol. 2-[Bis(p-fluorophenyl)methoxy]ethylamine hydrochloride is obtained. Its melting point is 170°–172° C.

The N-{2-[bis(p-fluorophenyl)methoxy]ethyl}-acetamide, used as a starting material, is prepared as follows:

A mixture of 25.4 g (0.1 mole) of bis(p-fluorophenyl)methyl chloride, 10.3 g (0.1 mole) of N-(2- hydroxyethyl)acetamide (prepared according to F. J. McQuillin et. al., J. Chem. Soc. 1955, 2966), 14 g of potassium carbonate and 100 ml of benzene is refluxed for 5 hours. After cooling, the reaction mixture is poured into water. The aqueous layer is extracted with dichloromethane and the combined organic layers are dried over potassium carbonate and concentrated by evaporation of solvent. The residue is crystallised from toluene. N-{2-[B is(p-fluorophenyl)methoxy]ethyl}-acetamide, m.p. 112°–113.5° C., is obtained.

EXAMPLE V

Using the procedure described in Example IV but substituting an equivalent amount of N--{-2-[0-chloro-α-(p-fluorophenyl)benzyloxy]e-thyl}acetamide for the N-{2-[bis(p-fluorophenyl)methoxy]ethyl}acetamide and maleic acid for the hydrogen chloride, there is obtained 2-[0 -chloro-α-(p-fluorophenyl)benzyloxy]ethylamine hydrogen maleate, which is crystallised from ethanol. Its melting point is 123°–123.5° C.

The amide starting material is prepared in the same way as described for the amide starting material in Example IV.

EXAMPLE VI

A solution of 1,2 g (0,0043 mol) of 2-[bis-(p-fluorophenyl)methoxy]acetamide in 10 ml of anhydrous tetrahydrofuran was added at room temperature to a suspension of 0,2 g (0,0043 mol) of lithium aluminiumhydride in 15 ml of anhydrous tetrahydrofuran. The reaction mixture was refluxed for 3 hours. The mixture was then cooled, decomposed with water and extracted with diethyl ether. The ethereal phase was extracted with 0,5N hydrochloric acid; the extract was made alkaline again with sodium hydroxide and extracted with diethyl ether. The extract was dried over sodium sulphate and concentrated. A solution of maleic acid in diethyl ether was added and the precipitate, consisting of 2-[bis(p-fluorophenyl)methoxy]-ethylamine hydrogen maleate, was filtered off and crystallised from a mixture of methanol and diethyl ether. Melting point 126°–127° C.

The amide starting material was prepared as follows. 23 g (0,083 mol) of 2-[bis(p-fluoropheny)methoxy] acetic acid was shaken with 4,47 g (0,083 mol) of sodium methoxide in 200 ml of methanol. The methanol was distilled off and the residue, consisting of the sodium salt of 2-[bis(p-fluorophenyl)methoxy] acetic acid was suspended in a small amount of dimethylsulphoxyde after which 38 g of methyl iodide was added. The reaction mixture was kept standing for 17 hours at room temperature and then water was added. The mixture was extracted with diethyl ether. The extract was dried over sodium sulphate and the ether was distilled off. The residue consisted of 2-[bis(p-fluorophenyl)methoxy] acetic acid methyl ester. The product was dissolved in 200 ml of methanol and a large excess of ammonia in methanol was added. The reaction mixture was kept standing for 18 hours at room temperature after which the solvent was distilled off. The solid residue was washed with a small amount of diethyl ether and twice crystallised from toluene. 2-[Bis(p-fluorophenyl)methoxy] acetamide was obtained. Melting point 110°–111,5° C.

EXAMPLE VII

A solution of 7,5 g (0,027 mol) of 2-[bis(p-fluorophenyl)-methoxy] acetonitrile in 10 ml of anhydrous tetrahydrofuran was added drop-wise at room temperature to a suspension of 1 g (0,027 mol) of lithium aluminiumhydride in 60 ml of anhydrous tetrahydrofuran. The reaction mixture was refluxed for 8 hours and it was decomposed and further treated as described in Example VI. 2-[Bis(p-fluorophenyl)methoxy]-ethylamine hydrogen maleate was obtained. Melting point 126°–127° C.

The nitrile starting material was prepared as follows. A mixture of 20 g (0,14 mol) of phosphorus pentoxide and 15 g of calcinated diatomaceous earth (trade-mark Hyflo) in 100 ml of anhydrous toluene was added drop-wise to a stirred and refluxing mixture of 14 g (0,05 mol) of 2-[bis(p-fluorophenyl)-methoxy] acetamide, 70 ml of toluene and 34 ml of triethylamine (dried over phosphorus pentoxide). The reaction mixture obtained was refluxed for 30 minutes, cooled and shaken with an aqueous sodium chloride solution. The organic phase was dried and concentrated and the oily residue was distilled. Boiling point 138°–145° C/0,65 mm Hg.

The invention includes within its scope pharmaceutical compositions comprising, as active ingredient, at least one of the therapeutically active ethers of general formula II, or a non-toxic acid addition salt thereof, in association with a pharmaceutically acceptable carrier.

The preparations may take any of the forms customarily employed for administration of therapeutic substances. Tablets and pills may be formulated in the usual manner with one or more pharmaceutically acceptable diluents or excipients, for example lactose or starch, and include materials of a lubricating nature, for example calcium or magnesium stearate. Capsules made of absorbable material, such as gelatin, may contain the active substance alone or in admixture with a solid or liquid diluent. Liquid preparations may be in the form of suspensions, emulsions, syrups or elixirs of the active substance in water or other liquid medium commonly used for making orally acceptable pharmaceutical formulations, such as liquid paraffin, or a syrup or elixir base. The active substance may also be made up in a form suitable for parenteral adminstration, i.e. as a suspension or emulsion in sterile water or an organic liquid usually employed for injectable preparations, for example a vegetable oil such as olive oil, or a sterile solution in water or an organic solvent.

The following Example illstrates pharmaceutical compositions according to the invention.

EXAMPLE VIII 50 g of 2-[bis(p-fluorophenyl)methoxy]ethylamine hydrochloride, 33 g of saccharis lactis, 87 g of amylum and 10 g of polyvinylpyrrolidone, are mixed and granulated with ethanol. The granulate is dried and mixed with .14 g of amylum and 6 g of a mixture of 8 parts of talcum, 1 part of Aerosil and 1 part of magnesium stearate. The mixture is then compressed into tablets of 200 mg, each containing 50 mg of the active substance.

I claim:

1. Diphenylmethoxyethylamines of the general formula

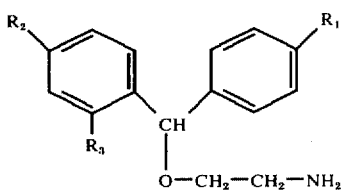

in which $R_1$ represents a fluoride, bromine or chlorine atom, $R_2$ represents a hydrogen or fluorine atom; and $R_3$ represents a hydrogen, fluorine or chlorine atom; with the provisos that $R_3$ is a hydrogen atom when $R_2$ is a fluorine atom, $R_1$ is a fluorine atom when $R_3$ is a chlorine atom and $R_1$ is a fluorine or bromine atom when $R_2$ and $R_3$ both are hydrogen atoms; and their non-toxic acid addition salts; and having dopamenergic activity.

2. The ethers according to claim 1 in which $R_2$ or $R_3$ represents a fluorine atom and $R_1$ represents a fluorine or chlorine atom.

3. The compound according to claim 1, 2-[bis(p-fluorophenyl) methoxy]ethylamine and its acid addition salts.

4. The compound according to claim 1, 2-[[p-chloro-α-(p-fluorophenyl) benzyl]oxy] ethylamine and its acid addition salts.

5. The compound according to claim 1, 2-[[o-fluoro-α-(p-fluorophenyl) benzyl]oxy] ethylamine and its acid addition salts.

* * * * *